US008268257B2

(12) United States Patent
Frost

(10) Patent No.: US 8,268,257 B2
(45) Date of Patent: Sep. 18, 2012

(54) PROCESS AND A DEVICE FOR TREATING OBJECTS

(75) Inventor: Robert Frost, Landshut (DE)

(73) Assignee: PTM Packaging Tools Machinery Pte. Ltd., Singapore (SG)

( * ) Notice: Subject to any disclaimer, the term of this patent is extended or adjusted under 35 U.S.C. 154(b) by 251 days.

(21) Appl. No.: 11/801,628

(22) Filed: May 10, 2007

(65) Prior Publication Data
US 2007/0269339 A1 Nov. 22, 2007

(30) Foreign Application Priority Data
May 19, 2006 (DE) .......... 10 2006 024 638

(51) Int. Cl.
A61L 2/00 (2006.01)
A61L 9/00 (2006.01)
A61L 2/04 (2006.01)
A61L 2/18 (2006.01)
A61L 2/20 (2006.01)
A61L 11/00 (2006.01)
C23F 11/00 (2006.01)

(52) U.S. Cl. ........ 422/297; 422/292; 422/295; 422/298; 422/300; 422/302; 422/1; 422/28; 422/33

(58) Field of Classification Search ............ 422/33, 422/292, 295, 297, 298, 300, 302, 1, 28
See application file for complete search history.

(56) References Cited

U.S. PATENT DOCUMENTS
4,207,286 A * 6/1980 Gut Boucher ................ 422/21
5,849,087 A * 12/1998 Kloberdanz et al. .......... 118/719
6,024,917 A * 2/2000 Kamstra ........................ 422/33
6,196,154 B1 * 3/2001 Baumecker et al. ..... 118/723 VE
6,354,427 B1 * 3/2002 Pickel et al. ............... 198/470.1
6,488,889 B1 * 12/2002 Stahlecker et al. ............ 422/22
6,627,163 B1 * 9/2003 Awakowicz et al. ..... 422/186.23
6,632,302 B2 * 10/2003 Fisher et al. .................. 148/640
6,902,928 B2 * 6/2005 Izvoztchikov et al. ..... 435/284.1
2001/0046464 A1 * 11/2001 Mykkanen .................... 422/302
(Continued)

FOREIGN PATENT DOCUMENTS
DE 199 16 478 A1 10/2000
(Continued)

OTHER PUBLICATIONS
English machine translation of DE 101 12 971.*
(Continued)

Primary Examiner — Regina M. Yoo
(74) Attorney, Agent, or Firm — Flynn, Thiel, Boutell & Tanis, P.C.

(57) ABSTRACT

Described is a process and an arrangement for the treatment of objects, in particular for sterilization, comprising at least one chamber for the joint take-up of at least two objects to be treated. A closing element is arranged to the opening of the chamber, which closing element is arranged in a moveable way in the arrangement for the purposes of opening and closing the opening. The chamber can be closed by means of the closing element in a vacuum-tight way, whereby no relative movement takes place between the closing element and the chamber in the closed state. It is provided that the minimum of two objects to be treated are inserted one after the other, and that the closing of the opening by means of the minimum one closing element takes place essentially on a continuous basis.

14 Claims, 4 Drawing Sheets

U.S. PATENT DOCUMENTS

| | | | |
|---|---|---|---|
| 2004/0146427 A1* | 7/2004 | Awakowicz et al. | 422/33 |
| 2005/0126118 A1* | 6/2005 | Till | 53/167 |
| 2007/0062911 A1* | 3/2007 | Siebels | 218/136 |
| 2008/0032059 A1* | 2/2008 | Zimmerer et al. | 427/458 |

FOREIGN PATENT DOCUMENTS

| | | |
|---|---|---|
| DE | 101 12 971 | 9/2002 |
| EP | 0452780 A2 | 10/1991 |
| JP | 2001301721 A * | 10/2001 |
| WO | WO 98/01344 | 1/1998 |
| WO | WO 2005044317 A2 * | 5/2005 |
| WO | WO 2006/010509 A2 | 2/2006 |

OTHER PUBLICATIONS

English translation of JP 2001301721.*
French Patent Office Search Report dated Mar. 26, 2010 (5 pages).

* cited by examiner

PROCESS AND A DEVICE FOR TREATING OBJECTS

BACKGROUND AND SUMMARY OF THE INVENTION

The present invention relates to a process and an arrangement for the treatment of objects, in particular for sterilization, comprising at least one chamber for the joint take-up of at least two objects to be treated, also comprising a minimum of one sealing element arranged to the opening of the chamber, which sealing element is arranged in a moveable way in the arrangement for the purposes of opening and closing the opening, whereby the chamber can be closed by means of the closing element in a vacuum-tight way, and whereby the closing element is arranged in the closed state to the chamber in such a way that no relative movement takes place between the closing element and the chamber.

The present invention relates further to a process for sterilizing a minimum of two objects to be sterilized in a joint chamber, which can be closed by means of a minimum of one closing element in a vacuum-tight way, whereby no relative movement takes place between the closing element and the chamber in the closed state.

Attention is brought to the fact that the definition "vacuum-tight" is not to be taken literally, but rather is defined on the basis of the process carried out in the chamber. The demands made on the seals are hereby essentially dependent on the required pressure in the chamber as well as on the level of a tolerable leakage of air.

An arrangement of the above mentioned type is prior art in German published patent application DE 199 16 478 A1. A round runner for the plasma sterilization of receptacles is described. The round runner comprises for example 50 chambers for taking up one receptacle each. The quantity produced by the round runner lies in the range of 20,000 receptacles per hour. Each chamber fixed to the round runner comprises a releasable base plate, which can be moved downwards. In order to load the chamber, a receptacle is placed on the released base plate, which is then moved upwards again until the plate touches the remaining chamber walls and the chamber is sealed. During the rotation of the round runner, the base plate moves together with the chamber, so that no relative movement takes place between the closing element and the chamber. The base plate is moved downwards again to open the chamber only at the end of the treating process, so that the receptacle can be removed.

Arrangements of this type are not only applied for plasma sterilization, but also for a process of the above mentioned type. A process of this type is known in German published patent application DE 101 12 971 A1. The disclosed process permits an effective sterilization of objects in the round runner, without a plasma having to be ignited. The effectiveness can be hereby improved.

An arrangement of this type has in particular the advantage that a very high production of objects is achievable due to the continuous way the machine operates, for example in the range of 30,000 objects per hour. Disadvantageous hereby is, however, that a very large number of chambers for taking up the objects have to be provided. The standard number of chambers is between 50 and 100. A set of valves is necessary for each chamber, in order to connect this chamber with the various supply and evacuation devices for the individual procedural steps. The entire arrangement requires a great amount of installation space, as the diameter of the round runner is extremely large due to the large number of chambers.

In the past, attempts have been made to optimize such arrangements by applying a number of objects, for example two or three, simultaneously in each chamber of the round runner. This leads to a light reduction in the number of chambers while maintaining the production performance, but the feed and removal of the objects to be treated cannot take place continuously. In an installation which transports the objects continuously, the removal of two objects simultaneously causes a discontinuity, which must be then be compensated for by a subsequent holding time. Because of this caused discontinuity, a discontinuous procedure of this type is fundamentally disadvantageous.

It is an object of the present invention, while maintaining the advantage of the continuous modus of operation, to reduce the number of necessary chambers and thus to simplify the arrangement and reduce the required installation space.

This object has been achieved in accordance with the present invention in that a minimum of two objects to be treated are inserted into the chamber one after the other, and in that the opening is essentially continuously closable by means of at least one closing element.

The feature of the essentially continuous closing of the opening is hereby to be understood in that the closing can take place in a phase comprising a number of steps, or continuously without steps. For this purpose, a number of rigid closing elements for a step-by-step closing of the opening in a number of stages can be arranged to the opening of the chamber. It can also be provided that a flexible closing element for continuous closing of the opening is arranged to the opening of the chamber.

The object of the present invention has been achieved in regard to the process in that the minimum two objects are inserted to the chamber one after the other, and in that the chamber is partly closed after the insertion of each object, and in that the chamber is closed in a vacuum-tight way and evacuated after the last object is inserted, and in that the vapour mix of gaseous hydrogen peroxide and gaseous water flows into the chamber in less than 8 seconds (in the following shortened to s), so that a condensation layer forms on all the accessible surfaces of the objects and the chamber, which condensation layer sterilizes the surfaces, and in that a renewed evacuation of the chamber begins at latest three seconds after the formation of the condensation layer, whereby the pressure of the chamber is lowered below the vapour pressure of the hydrogen peroxide thus resulting in the removal of the condensation layer, and in that the chamber is flooded with a sterile gas, and in that the chamber is opened essentially continuously and the objects can thus be removed one after the other from the chamber.

The advantage is achieved hereby in that the number of chambers can be reduced to between one and ten, without compromising on the continuous production of approximately 20,000 to 40,000 objects per hour. As a result of the reduced number of chambers, the arrangement requires significantly less installation space. In addition the supply of low pressure and hydrogen peroxide vapour mix to the chamber is simplified. Although the arrangement operates continuously, all objects inserted into a joint chamber are simultaneously at the same procedural step with regard to the treating process being carried out.

It should be expressly stated at this point that the described arrangement is in particular suitable for the described sterilization process, but is by no means limited to this process. The arrangement is just as ideally suitable for a plasma sterilization or for coating objects with plasma. Particularly advantageous is the application of the arrangement for treating bottles or other receptacles to be filled.

It is advantageous when a number of objects to be treated are inserted one after the other in at least two chambers, whereby the chambers are arranged to a chamber wheel which is driveable at a constant circumferential speed. Depending on the process to be carried out in the arrangement, two or three or several more chambers can be arranged to the chamber wheel. For the described sterilization process, three evenly distributed chambers on the circumference of the chamber wheel are advantageous.

In international patent application WO 2006/010509 A2 an air lock comprising a number of chambers arranged to a chamber wheel for the conveying of objects into a large treatment chamber. The chambers of the chamber wheel are successively evacuated to the pressure level of the treatment chamber while the chamber wheel is rotating. In the case of this airlock, continuous opening of the chambers is provided as a basic feature. However, in the case of this air lock there is no movable closing element, which, in the closed state, does not exert a relative movement in relation to the chamber. Instead, the chamber wheel of the air lock is surrounded by a stationary housing wall, in which two openings for filling and emptying the chamber are arranged. The chambers of the chamber wheel are surrounded by sealing elements which slide along the housing wall. The chambers, rotating with the chamber wheel, execute a relative movement to the housing wall closing the chambers, whereby a high level of wear occurs. It is necessary to change the sealing elements often. Each chamber of the air lock can take up two objects, which are, however, inserted simultaneously and not one after the other.

For a plasma treatment process or for the above described sterilization process it is advantageous when the arrangement comprises at least one central pump station for evacuating the chambers of the chamber wheel, which is connectable to all chambers one after the other in timed sequence, whereby each central pump station is connected at any one time to a maximum of one chamber. The central pump station can thus be optimized to the chamber size and to the required vacuum. As a result of the connection of at most one chamber with the central pump station, the situation is avoided whereby the vacuum level in the chamber originally connected with the pump station is affected because a second chamber is connected up to the same pump station.

It is advantageous to adapt the number of the chambers arranged on the chamber wheel to the process being carried out. The circumferential speed of the chamber wheel should be advantageously so chosen that a circulation time for one revolution arises, which essentially corresponds to the product out of the number of chambers, multiplied by the time a chamber is connected with a central pump station during one revolution of the chamber wheel. This results in the at least one central pump station being loaded very consistently and functioning with a high efficiency.

For the described sterilization process it is advantageous when an evaporator for an aqueous hydrogen peroxide solution is arranged to each chamber of the arrangement, which evaporator is applied in particular to the chamber wheel. By means thereof, a predetermined amount of an aqueous hydrogen peroxide solution can be very simply totally evaporated for each chamber at the required point in time, and fed to the respective chamber without the need for a carrier gas flow. For the described sterilization process it is advantageous when a vapour mix comprising a hydrogen peroxide concentration of approximately 14 to 59 percent regarding weight, preferably approximately between 25 and 50 percent regarding weight, and in particular comprising a hydrogen peroxide concentration of between 30 and 35 percent regarding weight is fed into the chamber. Due to the complete vaporization of a pre-measured amount of an aqueous hydrogen peroxide solution, it is necessary that the applied aqueous hydrogen peroxide solution has the same hydrogen peroxide concentration which the vapour mix flowing into the chamber should have.

It is advantageous, that the vapour mix flows into the chamber in less than 4 s, in particular less than 2 s. As a result of the rapid flow of the vapour mix into the chamber, an abrupt, essentially adiabatic expansion of the vapour mix takes place, which leads to a high level of cooling of the vapour mix. The vapour mix is thus over-saturated, so that condensation takes place on all exposed surfaces of the objects and of the chamber. This condensation also takes place abruptly, so that the condensation layer is heated to a great degree by the released evaporation enthalpy, thus leading to an "activation" of the hydrogen peroxide. The sterilization of the surfaces thus takes place practically in the moment of condensation. The chamber is evacuated again directly after the condensation formation, and the condensation layer is removed by lowering the pressure in the chamber below that of the vapour pressure of the condensed hydrogen peroxide.

The pumping out of the condensation layer takes place without any significant acting time directly after condensation, so that the condensation layer, warmed by the evaporation enthalpy, does not cool down by means of heat conduction to the surfaces of the objects and of the chamber. It is advantageous that the evacuation for removing the condensation layer is completed within 20 s, in particular within 10 s, after the vapour mix begins flowing in. This can prevent an excessive heat conduction of the condensation layer to the surfaces, so that the condensation layer can be very easily evaporated during evacuation and drawn off. The pressure in the chamber during evacuation to remove the condensation layer is preferably lowered to below 5 hectopascal (shortened in the following to hPa). The given pressure value corresponds to the absolute pressure in the chamber. The pressure can advantageously be lowered to below 1 hPa, in particular to below 0.35 hPa. The lower the pressure in the chamber during removal of the condensation layer, the less rest amount of hydrogen peroxide remains on the surfaces of the objects. Too large a rest amount of hydrogen peroxide on the objects can be disadvantageous for the further application of the objects.

BRIEF DESCRIPTION OF THE DRAWINGS

These and further objects, features and advantages of the present invention will become more readily apparent from the following detailed description thereof when taken in conjunction with the accompanying drawings wherein.

DETAILED DESCRIPTION OF THE DRAWINGS

Figure 1:
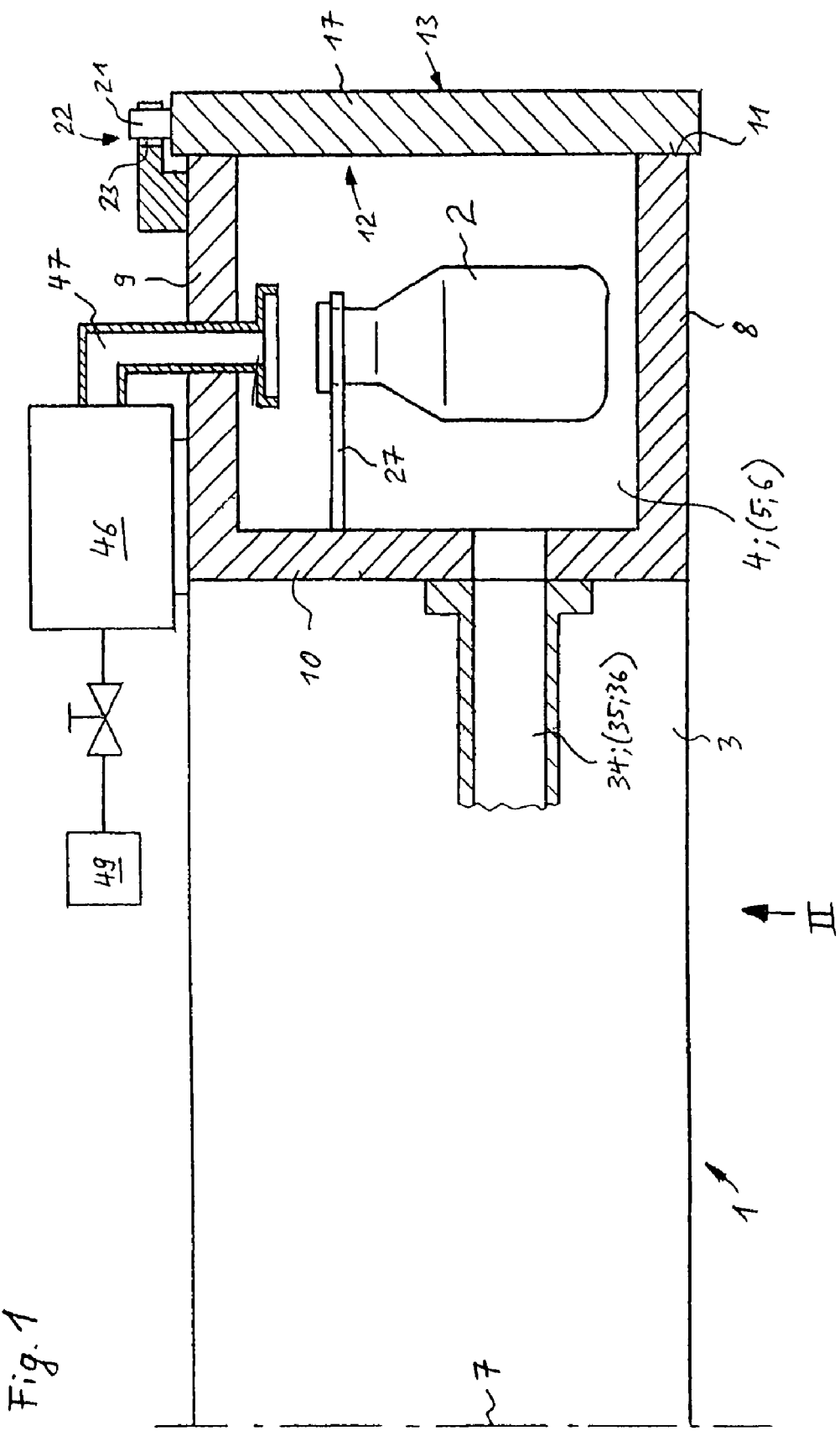
FIG. 1 shows an axial intersection of a chamber wheel of the arrangement according to the present invention.
Figure 2:
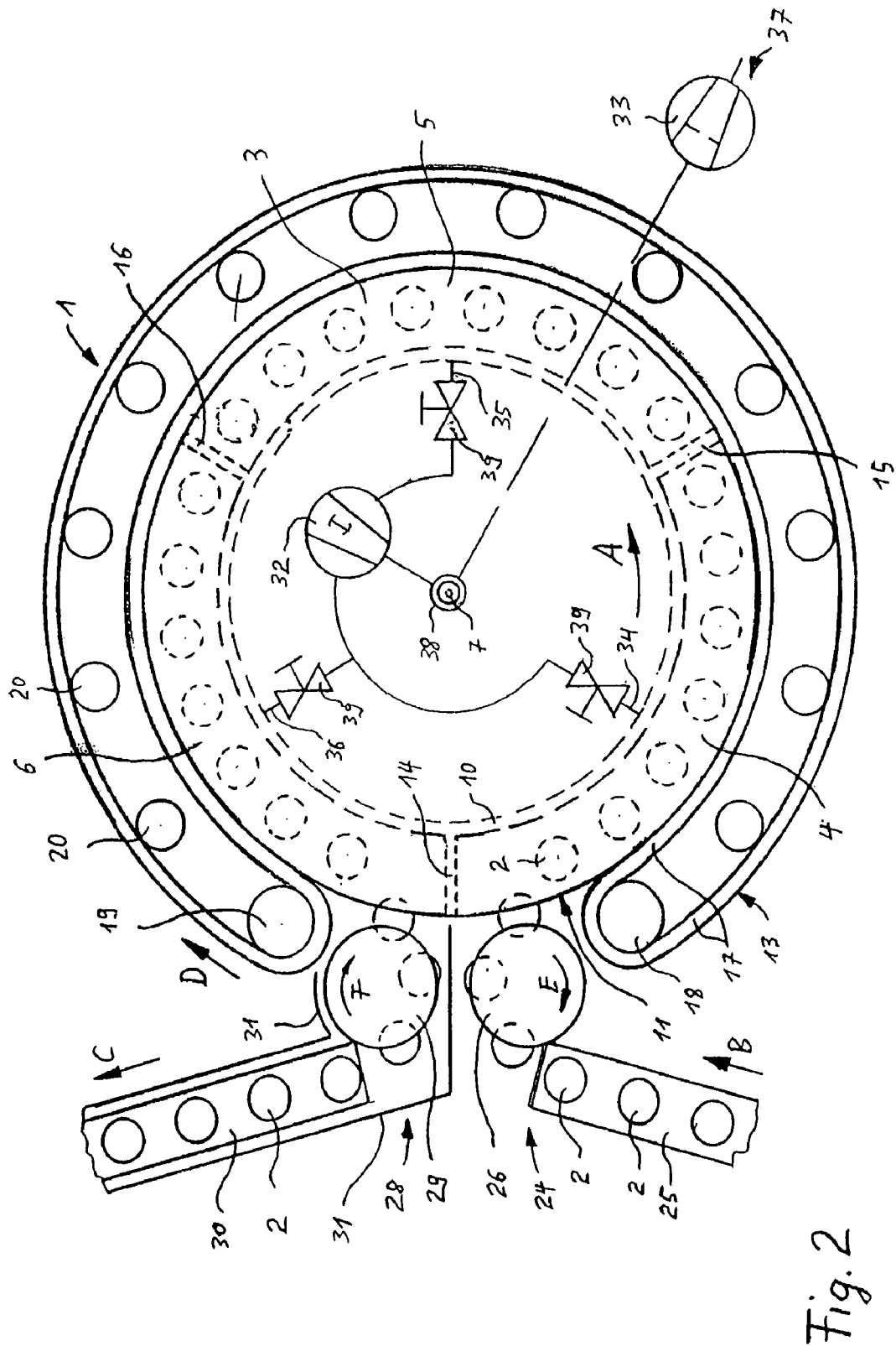
FIG. 2 shows a reduced view in the direction of the arrow II of FIG. 1 of the arrangement.

In the FIGS. 1 and 2 an arrangement 1 for treating objects 2 is shown. The objects 2 are shown schematically in FIG. 2 as circles and can be for example bottles, as indicated in FIG. 1, or also other receptacles for taking up drinkable fluids. The arrangement 1 includes essentially a chamber wheel 3 driven in rotational direction A comprising three chambers 4, 5, and 6 on its circumference. The chamber wheel 3 is driven during operation by a drive (not shown) and rotates at a constant speed in the rotational direction A around an axis 7.

The arrangement 1 is designed as a so-called round runner, in which the objects 2 to be treated are fed continuously in feed direction B and which are continuously transported away in removal direction C after treatment.

The chambers 4, 5 and 6 are each formed by a plane floor 8, a plane ceiling 9 and an essentially cylindrical inner wall 10. Each chamber 4, 5 and 6 comprises an opening 12 arranged on the cylindrical outer circumference 11 of the chamber wheel 3, to which opening 12 a closing element 13 is arranged. The boundaries of the chambers 4, 5 and 6 in circumferential direction of the chamber wheel 3 are effected by three partition walls 14, 15 and 16 extending from the inner wall 10 to the outer circumference 11 of the chamber wheel 3. The partition walls 14, 15 and 16 are flush with the outer circumference 11 of the chamber wheel 3 and extend thus to the closing element 13.

The closing element 13 is flexible and is arranged to the outer circumference 11 of the chamber wheel 3 in the form of an endless belt 17. The endless belt hereby loops two guiding rollers 18 and 19. The endless belt 17 is laid down by the guiding roller 18 on the outer circumference 11 of the chamber wheel 3 and runs synchronously with the chamber wheel 3 in rotational direction A. As a result of the synchronous run, no relative movement takes place between the endless belt 17 and the chamber wheel 3. The endless belt 17 is taken away again from the outer circumference 11 of the chamber wheel 3 at the guiding roller 19, and fed back to the guiding roller 18 by the guiding roller 19 against the rotational direction A in arrow direction D. A number of additional guiding rollers 20 can hereby be provided, which ensure the guidance of the endless belt 17.

The endless belt 17 consists preferably at least on the surface facing the chamber wheel 3 of an elastomer material. As a result additional seals can be omitted in the areas in which the endless belt 17 is disposed on the floor 8, the ceiling 9 and the partition walls 14, 15 and 16 of the chamber wheel 3. To reinforce the endless belt 17, which must withstand a load caused by the pressure difference between the surrounding pressure and the vacuum in the chamber 4, 5 and 6, reinforcement elements can be provided in the endless belt 17. These reinforcement elements can for example be formed by a number of rods 21 which are arranged adjacently and parallel to the axis 7. As a result the endless belt 17 becomes stable in relation to load due to the differences in pressure, its flexibility in longitudinal direction, which is important for an exact guiding around the guiding rollers 18 and 19, is however practically not impaired. Alternatively the endless belt 17 could be formed as a link belt by a number of movably connected but in themselves rigid linking elements.

In order to drive the chamber wheel 3 in rotational direction A, a drive is arranged to the chamber wheel in a way not shown. The endless belt 17, under slight pre-tension, can be disposed by means of the guiding rollers 18 and 19 on the outer circumference 11 of the chamber wheel 3 and taken along in rotational direction A. A separate drive for the endless belt 17 is in principle not necessary, as the endless belt 17 loops the chamber wheel 3 at a very large wrap angle. The endless belt 17 can thus be taken along by the friction on the outer circumference 11 of the chamber wheel 3 alone.

Alternatively, however, it can be advantageous to provide a positive locking connection 22 between the chamber wheel 3 and the endless belt 17. The positive locking connection 22 can advantageously be formed by an interlocking connection in the form of recesses 23 with the round rods 21 contained in the endless belt 17. The positive locking connection 22 can be optionally arranged to the chamber wheel 3, which means it can be arranged as show in FIG. 1, that is it can be arranged to the ceiling 9 of the chamber wheel 3. Alternatively the positive locking connection 22 can be applied to the floor 8 of the chamber wheel 3.

In a further embodiment of the present invention, it can be provided that the endless belt 17 has its own drive arranged thereto, in order to take some of the load from the drive of the chamber wheel. The drive of the endless belt 17 takes place advantageously via at least one of the guiding rollers 18, 19, 20 and is preferably designed as a torque regulated back-up drive, which, at an optional circumferential speed of the endless belt 17, transfers a defined drive moment thereto. The rotational speed of the endless belt 17 is thus preset by the chamber wheel 3, which ensures exactly that the endless belt 17 runs synchronously with the chamber wheel 3.

Each chamber 4, 5, 6 of the chamber wheel 3 runs in principle through three stages during one revolution, namely "load", "treat" and "de-load". In the depiction shown in FIG. 2, the chamber 4 is in the state "load", the chamber 5 in the state "treat" and the chamber 6 in the state "de-load". In between there is also an intermediary state, in which one chamber is simultaneously loaded and de-loaded. The chamber 6 comes into this state shortly after the snap shot depiction shown in FIG. 2.

In order to load the chamber 4 with the objects 2 to be treated, a loading device 24 is provided, to which the objects to be treated are fed in feed direction B, for example by means of a transport belt 25. The design of the loading device 24 is optional. The device 24 advantageously comprises an intake star 26 rotatable in arrow direction E, which intake star 26 takes over the objects 2 from the transport belt 25 by means of movable grippers and places them in the chamber 4. Holding means 27 for taking up the objects 2 could be provided within the chamber 4. It is alternatively possible to arrange the holding means 27 in a slidable manner in radial direction of the chamber wheel 3, so that the holding means 27 projects radially outwards over the outer circumference 11 of the chamber wheel 3 in the area of the loading device 24 and in this extended position takes up an object 2 from the loading device 24. In the course of the rotation of the chamber wheel 3 in rotational direction A, the holding means 27 can be moved radially inwards into its position, so that the object 2 reaches the interior of the chamber 4. For the present invention it is irrelevant how the loading device 24 is designed, and whether the holding means 27 are arranged in a movable manner inside the chamber wheel 3 or whether movable grippers are arranged to the loading device 24. Despite the optional design of the loading device 24, it is generally advantageous when the distance between the holding devices 27 in circumferential direction of the chamber wheel 3 is equidistant, so that all objects 2 are at an equal distance to one another in the chamber 4. This distance of the objects 2 to one another is defined as "pitch" and is, on the basis of the size of the objects to be treated, preferably chosen as small as possible. It is in particular advantageous when the distance between the last object—as seen in rotational direction A—of a chamber, for example chamber 5, and the first object 2 of the following chamber, for example chamber 4, is the same as the distance between the objects 2 inside the chamber, that is when the pitch is also unchanged at the partition walls 14, 15 and 16. This facilitates loading and unloading.

In the loading device 24 the objects 2 fed from the transport belt 25 are inserted one after the other in the chamber 4. The chamber 4 moves hereby at a constant speed in rotation direction A past the loading device 24. While the chamber 4 is being loaded with objects 2, the chamber 4 is closed by the closing element 13 in that area which has passed by the loading device 24 and is now located in the area of the guiding roller 18. The closing element 13, in the shown case the endless belt 17, is continuously disposed on the chamber wheel 3 and thus closes the chamber 4. The process of closing the chamber 4 by means of the closing element 13 begins therefore when the partition wall 15 has passed the area of the guiding roller 18, and ends when the partition wall 14 has passed the guiding roller 18. Only when the partition wall 14 has passed the guiding roller 18 is the chamber 4 completely closed and a treatment process can begin.

A particular advantage of this procedure is that the loading of the chamber 4 as well as the closing of the chamber 4 takes place practically simultaneously, whereby only a very short difference in time lies between the loading and the closing of the chamber 4. The closing of the chamber 4 is a continuous process by means of which the effectiveness of the arrangement 1 is increased to a great extent.

The part of the circulation time required for a full revolution which is available to the chamber 4 for the treatment of objects 2 is that part between when the partition wall 14 moves past the guiding roller 18 and the partition wall 15 arrives at the guiding roller 19. As soon as the front partition wall 15 of the chamber 4 reaches the guiding roller 19 during the rotation of the chamber wheel 3 in rotational direction A, the opening of the closing element 13 begins. The endless belt 17 is removed from the outer circumference 11 of the chamber wheel 3 by means of the guiding roller 19. The treatment of the objects 2 in the chamber 4 must be completed by this time. After moving past the guiding roller 19, the chamber 4 is open and can be unloaded by an unloading device 28.

The unloading device 28 can be similarly designed to the loading device 24. For example a take-out star 29—rotatable in arrow direction F—can be provided, which takes the objects 2 from the chamber 4 which is passing the unloading device 28 and transfers them to a transport belt 30, from which the treated objects 2 are transported away in removal direction C. In the case of a sterilization in the arrangement, it is advantageous to shield the unloading device 28 and the transport belt 30 by means of partition walls 31 in order to avoid a recontamination of the objects 2. The area within the partition walls 31 is provided with a slight overpressure, so that in the non-hermetically sealable areas between the loading device 28 and the chamber wheel 3, an air stream is constantly present flowing from the sterile into the non-sterile areas, which prevents germs from penetrating the sterile areas.

A number of the treating processes for which the arrangement 1 is suitable require at least temporarily a vacuum in the chamber 4, 5 or 6. Each chamber 4, 5 or 6 comprises for this purpose at least one vacuum connection 34, 35, 36, via which the respective chamber is connectable to one or more vacuum pumps 32 and 33. The two vacuum pumps 32 and 33 are connected in the shown case one after the other and form a central pump station 37. The shown central pump station 37 is designed with a pressure in the chamber 4, 5 or 6 of less than 5 hPa, and consists of a Roots pumps 32 and a rotary vane pump 33. The Roots pump is advantageously applied to the chamber wheel in a way that it rotates therewith and is connected in the area of the axis 7 of the chamber wheel 3 via a rotary feedthrough 38 with the rotary vane pump 33 which is applied in a stationary manner outside of the chamber wheel 3. The Roots pump 32 acts practically as a pre-condenser for the rotary vane pump 33, so that by means of the higher pressure downstream of the Roots pump 32, significantly lower demands are made on the rotary feedthrough 38.

It is now provided that the central pump station 37 is connectable to all chambers 4, 5 and 6 one after the other in a timed sequence, whereby the central pump station 37 is connected at any time with at most one of the chambers 4, 5, 6. For this purpose valves are provided between the vacuum connections 34, 35 and 36 and the central pump station 37. The valves are regulated by a control device (not shown) in such a way that at most one chamber 4, 5, 6 is simultaneously connected with the central pump station 37. In the shown case, the valves 39 of the vacuum connections 34 and 36 are closed, as the chambers 4 and 6 are opened for the purposes of loading and unloading. The valve 39 at the vacuum connection 35 of the chamber 5 can be opened, so that the chamber 5 is connected with the central pump station 37 and can be evacuated.

As already described, the chamber 4 is completely closed during the rotation of the chamber wheel 3, as soon as the partition wall 14 moves through the area of the guiding roller 18. Before the chamber 4 is connected with the central pump station 37 by means of opening the valve 39 at the vacuum connection 34, it is advantageous to close the valve 39 at the vacuum connection 35 and to disconnect the chamber 5 from the central pump station 37. This prevents air from the as yet not evacuated chamber 4 from flowing over into the already evacuated chamber 5 and impairing the vacuum already achieved there.

If in the case of the treatment process carried out in the arrangement 1, a number of procedural steps are involved in which the chamber 4, 5, and 6 must be evacuated, as is the case for example in the sterilization process described below, it is advantageous to provide a separate central pump station 37 for each evacuation process. The separated central pump stations 37 can be optimized hereby in relation to the number and type of the pumps used according to the required level of low pressure.

The circulation speed at which the chamber wheel 3 is driven in rotational direction A is so chosen that a circulation time for one revolution is given, which essentially corresponds to the product out of the number of chambers—in the present case 3—multiplied by the time a chamber 4, 5, 6 is connected with the central pump station 37 during one revolution of the chamber wheel 3. This results in the at least one central pump station 37 being loaded very consistently and functioning very efficiently. If for example 3 s are necessary for the evacuation of the chamber 5, in order to achieve the desired vacuum, the circulation time for the chamber wheel 3 with the shown three chambers 4, 5 and 6 advantageously 9 s. If four chambers are provided on a chamber wheel 3, in a way not shown, the circulation time should amount to 12 s if a chamber needs 3 s for the evacuation.

Figure 3:
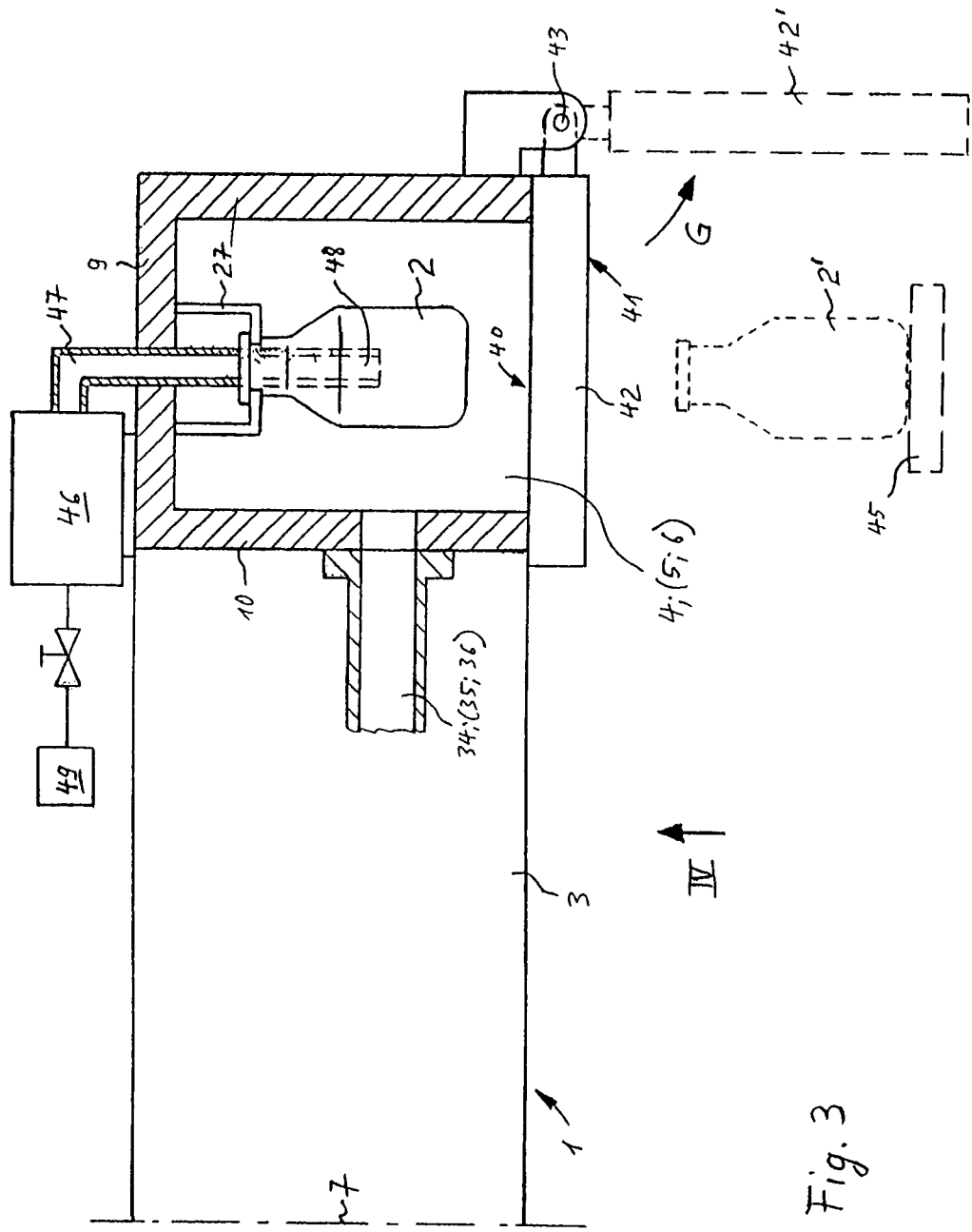
FIG. 3 shows a view similar to FIG. 1 of another embodiment of a closing element of the arrangement.
Figure 4:
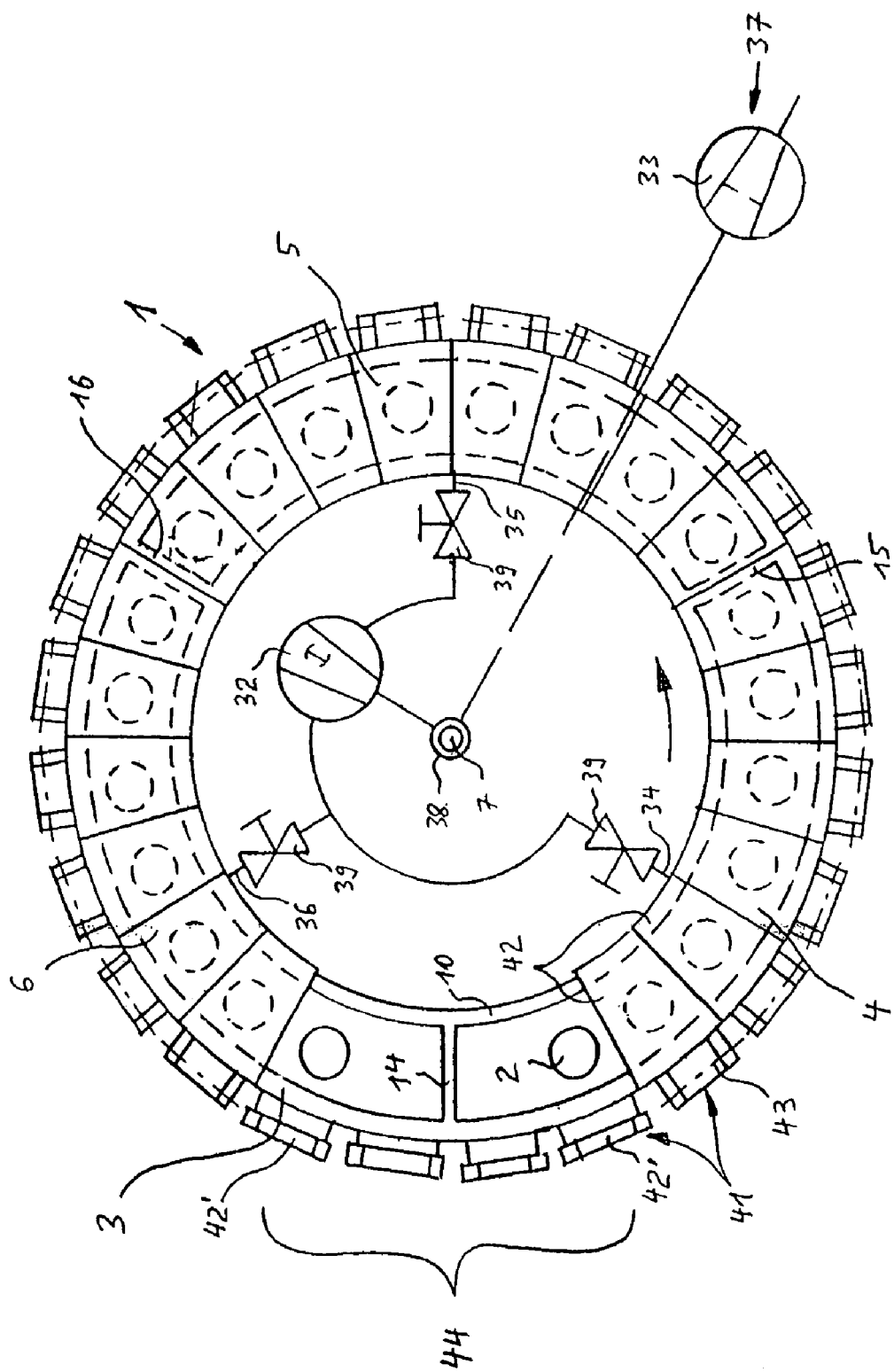
FIG. 4 shows a reduced view in the direction of the arrow IV of the arrangement according to FIG. 3.

In FIGS. 3 and 4 a variation of an arrangement 1 for treating objects 2 is shown, which in turn comprises a chamber wheel 3 with three chambers 4, 5 and 6 evenly distributed on the circumference. The chamber wheel 3 is in turn driveable around the axis 7 in circulation direction by means of a drive (not shown). The chambers 4, 5 and 6 are each again separated from one another by means of partition walls 14, 15 and 16.

The chambers 4, 5 and 6 comprise, in contrast to the openings 12 shown in FIGS. 1 and 2 and directed radially outwards, each an opening 40, which is aligned axially to the chamber wheel 3. The loading and unloading thus takes place not in radial direction but rather in axial direction of the chamber wheel 3, for example from below. A number of rigid closing elements 41 are arranged to the openings 40 of the chambers 4, 5 and 6, so that each chamber 4, 5 and 6 can be closed gradually in several stages. The closing elements 41 can for example be designed as flaps 42 which can be swiveled around an axle 43. The flaps 42 can be swiveled open in arrow direction G for loading and unloading and can be brought into the position 42' shown by a broken line. Advantageously one closing element 41 is assigned to each object 2, which closes the section of the opening 40 which is necessary for the insertion and the removal of this object 2.

The loading and unloading of the chamber wheel 3 takes place in an area shown in FIG. 4 with the reference number 44 in an optional way. Transport belts for feeding and removing the objects 2 can again be provided hereby. A loading device 45 is denoted by a broken line in FIG. 3, which, when the flap 42' is open, can insert an object 2' from below in axial direction of the chamber wheel 3 into the chamber 4. The open flaps 42' of the closing elements 41 can also be seen in FIG. 4 in the loading and unloading area 44.

The objects 2 to be treated are fed continuously to the arrangement 1 and inserted one after the other by means of the loading device 45 into the chamber 4. The chamber wheel 3 rotates hereby at a constant rotational speed in rotational direction A passed the loading device 45. After the object 2 has been inserted in the chamber 4, the respective closing element 41 relating to this object 2 is closed. The closing of the opening 40 of the chamber 4 takes place hereby only in an essentially continuous way, namely step by step in a number of stages. The closing elements 41 are hereby so formed that in the closed state they are disposed closely together and can vacuum-seal the chamber 4, 5 and 6. This can for example be realized in that each flap 42 lies closely adjacent to the next flap 42. In a way not shown, sealing elements can of course be provided at the partition points between the chamber 4, 5, 6 and the flaps 42, as well as between the flaps 42 themselves.

Identical to the embodiment shown in FIGS. 1 and 2, at least one or a number of central pump stations 37 can also be provided in the embodiment shown in FIGS. 3 and 4. The placing and the control are advantageously also designed as described above, so that a repeat description can be omitted at this point.

As already mentioned, the arrangement 1 is not limited to one particular process, it is however particularly suitable for a specific process for sterilizing objects 2. This sterilizaton process is described in more detail below.

The process for sterilizing objects 2 can begin as soon as all objects 2 are inserted into the respective chamber 4, 5, 6 and the chamber, for example chamber 4, as described above, is vacuum-tight. The vacuum-tight chamber 4 is evacuated to a pre-evacuation pressure, which can lie in the range of below 300 hPa, below 100 hPa or below 40 hPa. The pre-evacuation pressure can influence the sterilization effect and should be chosen with the overall process in view. The pre-evacuation takes place advantageously with a first central pump station 37, which is adapted in its performance to the desired pre-evacuation pressure and the chosen chamber size.

In the pre-evacuated chamber there is an influx of a vapour mix consisting of gaseous hydrogen peroxide and gaseous water in less than 8 s into the chamber 4, so that a condensation layer forms on all accessible surfaces of the objects 2 and of the chamber 4, which condensation layer sterilizes the surfaces. It is hereby provided that a pre-determined amount of aqueous hydrogen peroxide solution is evaporated completely, to obtain a vapour mix of hydrogen peroxide and water, which has the same hydrogen peroxide concentration as the aqueous hydrogen peroxide solution. The hydrogen peroxide concentration in the aqueous solution and in the vapour mix lies in the range between 14 and 59 percent regarding weight. Advantageously also are hydrogen peroxide concentrations between 25 and 50 percent regarding weight and in particular between 30 and 35 percent regarding weight.

To create the vapour mix an evaporator 46 can be provided, from which the vapour mix is conducted via distributor pipes 47 into the chamber 4, 5, 6. It is hereby advantageous to arrange to each chamber 4, 5 and 6 its own evaporator 46, which can for example be mounted directly onto the chamber wheel 3 and which rotates with the chamber wheel 3. Depending on the desired distribution of the vapour mix, it can also be advantageous to permit a distributor pipe 48, as shown in FIG. 3, to project into the interior of each object 2, here shown as a bottle. The pre-determined amount of aqueous hydrogen peroxide solution is fed advantageously to the evaporator 46 from at least one container 49.

The vapour mix flows abruptly into the chamber 4 without the aid of a carrier gas, so that the vapour mix cools down very strongly due to an essentially adiabatic expansion. The abrupt flow-in of the vapour mix should take place in any case in less than 8 s, advantageously in less than 4 s and in particular in less than 2 s. The cooling down caused by the abrupt expansion of the vapour mix effects an over-saturation of the vapour mix and an equally abrupt condensation on all accessible surfaces of the objects 2 and of the chamber 4. The condensation layer forming on the surfaces is heated to a large degree by means of the released evaporation enthalpy. The heating of the condensation layer effects a so-called "activation" of the hydrogen peroxide, whereby the hydrogen peroxide develops its sterilizing effect. The sterilization takes place practically in the moment of the condensation, so that a further acting time for the condensation layer on the surfaces is not necessary and the condensation layer can be pumped out of the chamber 4 by means of re-newed evacuation. The post-evacuation to remove the condensation layer should begin no later than 3 s after the formation of the condensation layer, whereby the pressure in the chamber 4 is lowered below the vapour pressure of the hydrogen peroxide. As a result the condensation layer of water and hydrogen peroxide evaporates again and the hydrogen peroxide can be removed. Depending on the pressure in the chamber 4 during post-evacuation, a rest amount of hydrogen peroxide remains on the surfaces, which rest amount also decreases with decreasing pressure during post-evacuation. Depending on the acceptable rest amount it is advantageous to lower the pressure during post-evacuation for removing the condensation layer to below 5 hPa, in particular below 1 hPa and, in order to achieve very low rest amounts, also below 0.35 hPa. Because of the different level of pressure in comparison to the pre-evacuation process, it is advantageous to apply a separate central pump station 37 for the post-evacuation process.

The rest amounts remaining on the surfaces of the objects 2 can also be influenced by the temperature of said objects 2. The higher the temperature, the lower is the rest amount. It can therefore be advantageous to warm the objects, and of course accordingly the chamber 4, before or during insertion, to a temperature above the room temperature in the order of magnitude of 60° C., preferably to a temperature of between 25° and 40° C. In addition to a pre-warming of the objects 2, a pre-warming of the chamber 4 is also necessary, so that too much vapour mix does not unnecessarily condense on the chamber walls. The objects 2 should rather tend to be somewhat colder than the chamber walls.

The process must inevitably proceed at a relatively high speed, so that as little warmth as possible dissipates from the formed condensation layer to the comparatively colder surfaces of the objects 2 and of the chamber 4. The dissipation of warmth from the condensation layer to the surfaces cools the condensation layer down, so that subsequently it does not evaporate well during post-evacuation. It is therefore advantageous that the evacuation for removing the condensation layer is completed within 20 s, in particular within 10 s after the vapour mix has begun to flow in.

After the condensation layer has been extracted by means of post-evacuation, the chamber 4 is flooded with a sterile gas, for example air or nitrogen. The sterile gas can be stored in a sterile air tank assigned to the arrangement 1.

With the flooding of the chamber 4 by the sterile gas, the sterilization process is thus completed and the chamber 4 is essentially continuously opened and the objects 2 are removed one after the other from the chamber 4.

For the described sterilization process it is very advantageous to arrange three chambers 4, 5, 6 on the chamber wheel. The process is executed in time-delayed rotation in one chamber 4, 5, 6 after the other. In the above described sterilization process, the procedure of the post-evacuation for extracting the condensation layer is that section of the process which requires the most time. The arrangement 1 is designed accordingly around this post-evacuation time. The time for the post-evacuation for extracting the condensation layer lies advantageously in the area of between 3 s and 15 s, preferably in the area of between 4 s and 8 s. As already described above, the circulation time of the chamber wheel 2 is chosen as a product of this post-evacuation time and the number of chambers 4, 5, 6. From the circulation time and the desired production performance arises the overall number of objects 2 that the chamber wheel must take up. For example, a post-evacuation time of 4 s results in a circulation time with three chambers 4, 5 and 6 of 12 s. For a production performance of 36,000 objects 2 per hour, a chamber wheel 3 is required which can take up 120 objects 2. 120 objects on the chamber wheel 3 corresponds to 40 objects per chamber 4, 5, 6. The absolute size of the chamber wheel 3 then depends on the size of the objects 2 and the required pitch thereof.

The described arrangement 1 can be integrated without difficulty into a continuously operating installation, for example for producing and filling receptacles, as the loading and unloading of the arrangement 1 can take place in a strictly continuous way, so that absolutely no type of buffer or between-storage of the fed or removed objects is necessary. In contrast to standard round runners, the arrangement 1 has the distinctive feature that not all objects simultaneously located in the round runner are at a different, if only minimally different, stage of the process, but rather that all objects in a chamber 4, 5 or 6 find themselves at exactly the same stage in the treatment process. This occurs because the objects 2 are inserted into the chamber 4, 5 and 6 one after the other and are subsequently removed one after the other, but that in the intermediary phase of the treatment process all objects in the chamber 4, 5 and 6 are treated simultaneously.

The invention claimed is:

1. A moveable apparatus for treatment of objects, comprising:
    at least one chamber configured for temporary retention of at least two objects to be treated therein, the at least one chamber having an opening and at least one holder disposed therein for stabilization of objects within the at least one chamber, the at least one chamber comprising a portion of a chamber wheel which is moveable;
    at least one closing element adjacent the opening of and engageable with the at least one chamber, the at least one closing element being moveable and disposed to open and close the opening during movement of the moveable apparatus, creating a chamber opened state and a chamber closed state, wherein in the chamber closed state the at least one closing element forms at least a portion of a wall of the at least one chamber, the at least one chamber being configured to be closed air-tight by the at least one closing element, the at least one chamber and the at least one closing element moving in the at least one closed state at the speed of the chamber wheel, the at least one closing element being arranged in the chamber closed state of the at least one chamber such that no relative movement takes place between the closing element and the at least one chamber during movement of the chamber wheel; and
    a locking member connected to the at least one chamber and connected to the at least one closing element for attaching and locking said at least one closing element to said at least one chamber during operation of the moveable apparatus, the locking member comprising a rod attached to the at least one closing element.

2. The moveable apparatus of claim 1, wherein the at least one holder is disposed and configured to maintain objects in the at least one chamber in a non-moveable fashion relative to the at least one chamber.

3. The moveable apparatus of claim 1, wherein the at least one chamber has a sole opening for insertion and removal of objects into and from the at least one chamber.

4. An arrangement for treatment of objects, in particular for sterilization, comprising:
    at least one chamber for at least two objects to be treated, the at least one chamber having an opening therein;
    at least one closing element adjacent the opening of the at least one chamber, the at least one closing element being arranged in a moveable way in the arrangement for opening and closing the opening and in a closed state forming at least a portion of a wall of the at least one chamber, the at least one chamber configured to be closed vacuum-tight by the at least one closing element, and the at least one chamber comprising a portion of a chamber wheel which is moveable; and
    a locking connection mounted adjacent the at least one chamber and attached to the at least one closing element for locking the at least one closing element in place with respect to the at least one chamber during movement of the at least one chamber, the locking connection comprising a rod attached to the at least one closing element, and a connection member having a recess therein for engagement with the rod,
    the at least one closing element being arranged in the closed state of the chamber at least one such that no relative movement takes place between the at least one closing element and the at least one chamber during movement of the at least one chamber, the at least one chamber and the at least one closing element moving in the closed state at the speed of the chamber wheel, the at least two objects to be treated being insertable one after the other into the at least one chamber, and once inserted into the at least one chamber the objects being stabilized by a holder, and the opening being essentially continuously closable by the at least one closing element.

5. The arrangement according to claim 4, wherein a number of objects to be treated are insertable one after the other in at least two chambers, the at least two chambers being part of the chamber wheel which is driven at a constant circumferential speed.

6. The arrangement according to claim 5, wherein the chamber wheel comprises three chambers which are evenly distributed on the circumference of the chamber wheel.

7. The arrangement according to claim 5, further comprising at least one central pump station for evacuating the at least two chambers of the chamber wheel, which at least one central pump station is connectable with all at least two chambers one after the other in timed sequence, each central pump station being connected to at most one chamber at any one time.

8. The arrangement according to claim 5, wherein the at least one closing element is flexible.

9. The arrangement according to claim 8, wherein the at least one flexible closing element is an endless belt located at the outer circumference of the chamber wheel.

10. The arrangement according to claim 5, further comprising an evaporator, for vaporization of an aqueous hydrogen peroxide solution, fixed to each chamber.

11. The arrangement according to claim 10, wherein the evaporator is connected to the chamber wheel.

12. The arrangement according to claim 4, wherein the at least one closing element comprises flaps for closing the opening gradually in several stages, the flaps being disposed adjacent the opening of the at least one chamber.

13. The arrangement according to claim 4, wherein the at least one chamber has a sole opening for insertion and removal of objects into and from the at least one chamber.

14. The arrangement according to claim 4, wherein the holder is disposed within the at least one chamber and is configured to stabilize objects disposed within the at least one chamber so that the objects are not moveable relative to the at least one chamber.

* * * * *